United States Patent [19]

Watanabe

[11] Patent Number: 4,590,923

[45] Date of Patent: May 27, 1986

[54] ARTHROSCOPE-VIDEO CAMERA ASSEMBLY

[76] Inventor: Robert S. Watanabe, 11645 Wilshire Blvd., Ste. 701, Los Angeles, Calif. 90024

[21] Appl. No.: 486,026

[22] Filed: Apr. 18, 1983

[51] Int. Cl.$^4$ ............................................... A61B 1/06
[52] U.S. Cl. ......................................... 128/6; 354/62; 358/98
[58] Field of Search .................................... 128/4–8, 128/303.1, 371, 395; 312/209; 354/62; 358/98, 229, 249

[56] References Cited

U.S. PATENT DOCUMENTS

| | | | |
|---|---|---|---|
| 3,229,368 | 1/1966 | Tocchini | 312/209 |
| 4,028,730 | 6/1977 | Miller | 358/229 |
| 4,253,447 | 3/1981 | Moore et al. | 128/6 |
| 4,343,300 | 8/1982 | Hattori | 128/6 |
| 4,413,228 | 11/1983 | Feinborn | 354/62 |

FOREIGN PATENT DOCUMENTS 1262502  3/1968  Fed. Rep. of Germany .......... 128/6

OTHER PUBLICATIONS

"Miniature Black and White TV Camera for Endoscopy and Other Medical Applications", Berci, Bio-Medical Engineering, Apr. 1972.
"Fiber-Optics Couple Arthroscope to TV", NASA Tech Briefs, Fall 1980 vol. 5, No. 4.

*Primary Examiner*—Edward M. Coven
*Assistant Examiner*—Max F. Hindenburg
*Attorney, Agent, or Firm*—Keith D. Beecher

[57] ABSTRACT

An arthroscopic assembly in which a video camera is enclosed in a tubular sterile housing formed, for example, of stainless steel, and which may be autoclaved for multiple procedures. The assembly includes a arthroscope detachably plugged into a mounting bracket which, in turn, is plugged into a socket at the front end of the housing, so that the arthroscope may be changed during an operation to incorporate other arthroscopes of different lens angles without fear of contamination of the assembly. An arthroscopic light for the arthroscope is detachably plugged into the mounting bracket so that light therefrom passes through the mounting bracket to the arthroscope. The video camera enclosed in the housing is plugged into an electric socket at the rear end of the housing. The arthroscope itself does not include an eyepiece so it is shorter than the usual prior art arthroscopes, and it is optically coupled directly through the mounting bracket and through the socket at the front end of the camera housing to the video camera in the housing. A stand is provided which contains electric outlets for the arthroscope light and for the video camera. A sterile holder is provided on top of the stand on which the arthroscopic assembly may be placed when not in use. The stand may be positioned adjacent to the surgeon to make the arthroscopic assembly readily available to the surgeon so as to minimize the length of electric cords necessary for the arthroscopic light and for the camera.

13 Claims, 6 Drawing Figures

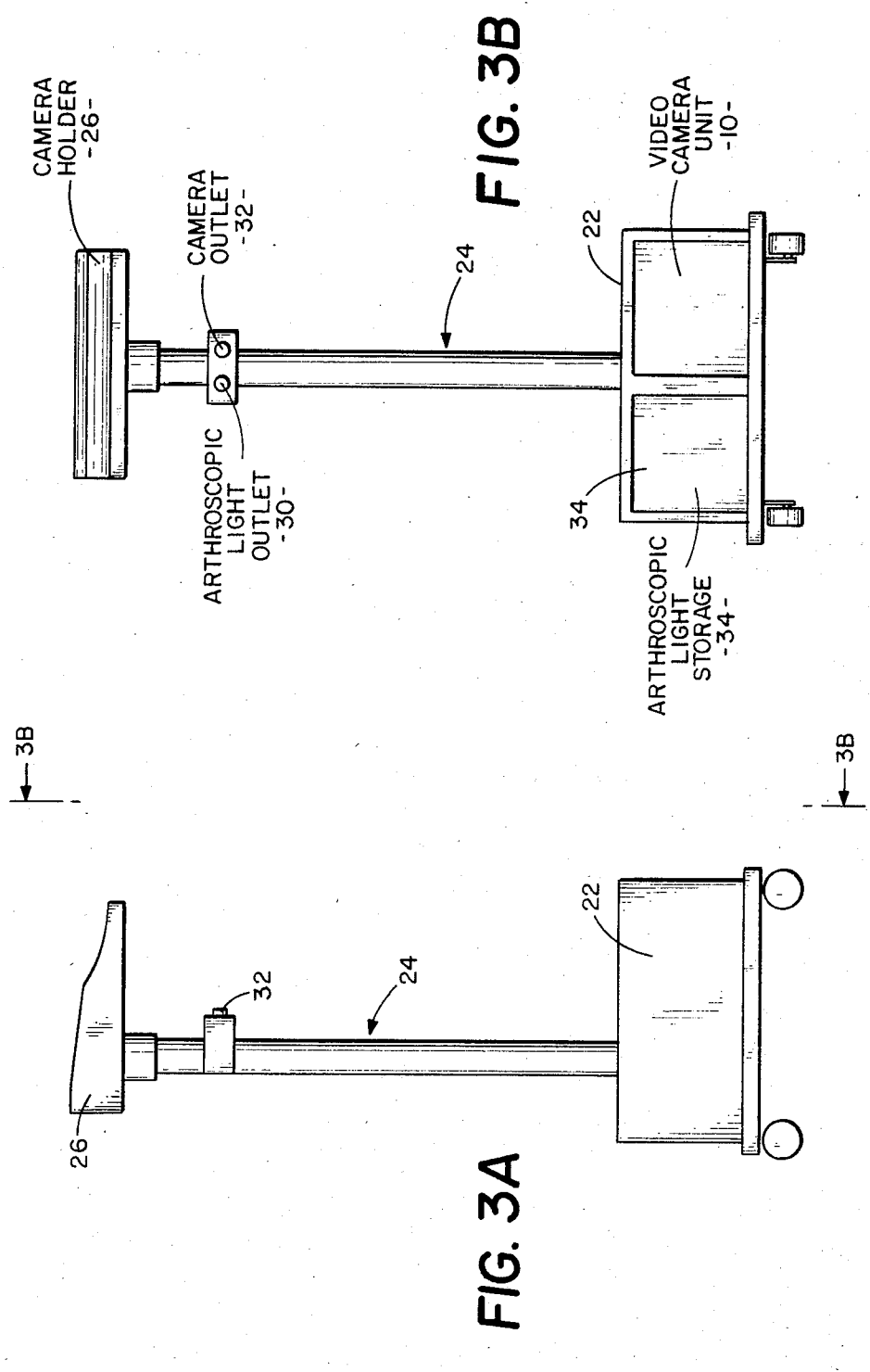

ARTHROSCOPE-VIDEO CAMERA ASSEMBLY

BACKGROUND OF THE INVENTION

Arthroscopy is a particular form of endoscopy which, in turn, is the art of examining the interior of a body cavity or hollow organ by the use of a thin tubular instrument known as an "endoscope". Endoscopes have been in common use since the early 20th Century. These instruments include a lens system, which may be conventional glass lenses within a rigid tube, optical glass fibers, and a lighting system by which light from an external source is conducted through the optical glass fibers. Endoscopes also commonly contain an irrigation system for introducing fluids, typically normal saline solution, to the region being examined. Endoscopes have been used for arthroscopic examination for about fifteen years. The development of arthroscopy and instruments adapted for arthroscopic examinations, known specifically as arthroscopes, are described in an article entitled "Arthroscopy of the Knee" by Robert W. Jackson, et al., Modern Orthopedic Monographs, 1976, published by Brune & Stratton, Inc. of New York.

The arthroscope, like the endoscope, is a long tube with a fiber optic light carrier which permits light to be transmitted down the tube into the body, and which further permits the doctor to view the area of the body adjacent to the distal end of the arthroscope. Arthroscopes can be particularly useful in observing the conditions inside the human body. One area of the human body which arthoscopic viewing can be extremely useful is in the knee. A surgeon frequently finds it highly desirable to view the postermedial compartment of the knee in order to observe conditions in the compartment and to view the cartilage adjacent to the compartment.

Arthroscopy procedures have been performed in North America for the past fifteen years, and have been heralded by many physicians, professional athletes, managers and trainers as wonder surgery. Their reasoning is sound because arthroscopic surgery can usually be completed in about an hour in a doctor's office, the only anethesia required being local, and the recovery time being minimal, in many cases only a few weeks. The surgeon uses the arthroscope to perform this type of surgery. The instrument, which works on the same principle as a telescope, contains a tube with a fiber optic light carrier that lights up the joint, and glass lenses that reflect the image back to the surgeon. Some arthroscopes provide direct viewing, and others allow for 30°–70° angles.

In recent years, arthroscopic surgery of the knee joint has become a rapidly expanding procedure in the field of orthopedic surgery. Since the introduction of arthroscopy into the United States about fifteen years ago, arthroscopists have proliferated at a rapid rate.

Video systems for arthroscopy have recently been developed in which the eyepiece of the arthroscope is optically coupled to a video camera, and the arthroscopic images are displayed on the screen of a cathode-ray monitor. Such systems are marketed, for example, by Stryker Corporation of Kalamazoo, Mich. The present invention is concerned with arthroscopic video systems, and the principal objective of the invention is to provide an improved arthroscopic video system and assembly.

There also have been rapid advances in the state of the art with respect to arthroscopic equipment since its initial introduction and the recent use of the video camera and cathode-ray monitor have added significantly to the ease of arthroscopic use. The main problem insofar as video systems are concerned, however, is that the original arthroscope is still being used in the prior art systems, and it is coupled to the modern video camera through its original eyepiece by means of a cumbersome adapter. In order to keep the camera unit sterile, it is the usual present-day practice to use a plastic bag tied to the arthroscope with a piece of string. This makes it difficult to change the various arthroscope, for example, from a 10° arthroscope to a 70° arthroscope, without the danger of contamination. There is also the danger of water leaking into the camera unit and causing damage.

The assembly of the present invention includes an arthroscope which is constructed to be used with a video camera and, for that reason, does not have an eyepiece. The arthroscope in the assembly of the invention plugs into a mounting bracket which, in turn, plugs into a socket at one end of a tubular video camera housing using a bayonet-type of plug so that the arthroscope may be optically coupled to the video camera within the housing. The arthroscope is detachable from the mounting bracket, and it can be changed to any one of several arthroscopes having either direct viewing, or 10°–30°–70° and even 90° viewing angles, this being achieved within a matter of seconds, without any danger of contamination.

In the prior art systems, it was necessary to remove a plastic cover from the anthroscope before such a change could be made, and when that happened, the eyepiece of the arthroscope became contaminated, all of which created problems in the operating room.

The removable arthroscope used in the assembly of the present invention is compact and economical, since it does not have an eyepiece. An arthroscopic light is detachably attached to the mounting bracket. The removable arthroscope in the assembly of the invention is detached from the mounting bracket at a point displaced from the attachment of the arthroscopic light to the mounting bracket, so that when changing the arthroscope, the light source is not affected, and the electric cord supplying light to the arthroscopic light does not have to be detached, as is the case in the usual prior art assemblies.

The video camera housing in the assembly of the present invention encases the video camera in a sterile container which eliminates the need for the plastic bag. In practice, the housing is first sterlized in an autoclave, and is then opened at one end and the camera is inserted into the housing through the open end. The open end of the housing is then closed. The arthroscope is then plugged into the mounting bracket which, in turn, is plugged into the socket at the forward end of the housing by means of the bayonet plug. The electric cord for the video camera is attached to an electric socket at the rear end of the housing and the video camera is plugged into the socket. An advantage of the assembly of the invention is that it does not require a plastic cover sheet for the camera and cord. Also, the arthroscope can be changed to provide different lens angles without any danger of contamination.

The entire video monitor and cabinet in the prior art video arthroscope system is large and cumbersome, and takes up significant space in the operating room. There is also the problem of having multiple cables coming over from the video and light units which add to the complexity of the system. At present, it is usual to provide a large boom which holds the cables up over the operating table. A further objective of the present invention is to modify the overall system to make the assembly more compact.

BRIEF DESCRIPTION OF THE DRAWINGS

FIG. 3A is a side elevation, and FIG. 3B is a front view (taken along the lines 3B—3B of FIG. 3A) of a stand for the arthroscopic unit, and for various ones of the video components shown in FIG. 1.

DETAILED DESCRIPTION OF THE ILLUSTRATED EMBODIMENT

Figure 1:
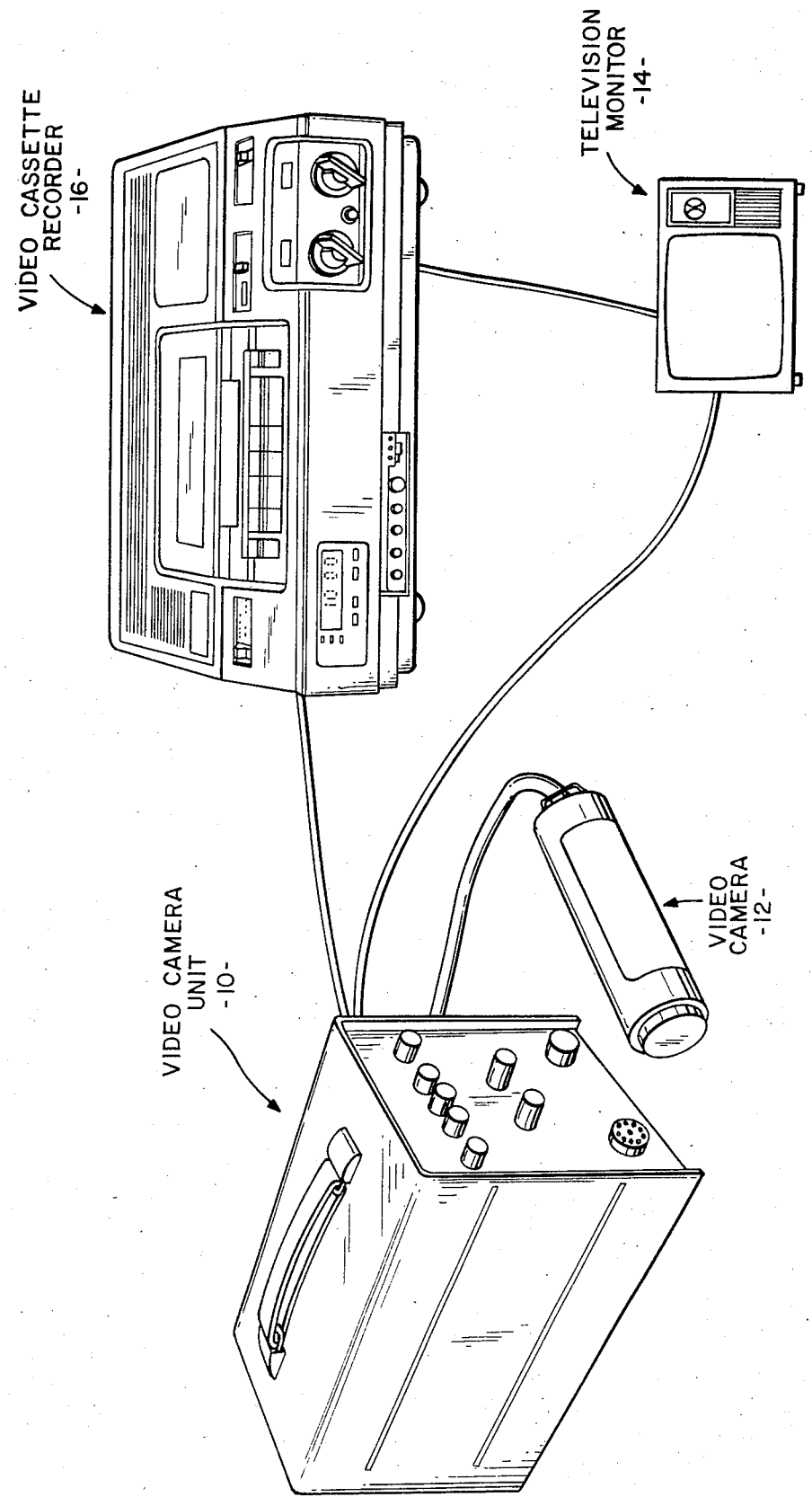
FIG. 1 is a representation of the various video components which may be used to enable arthroscopic images from an arthroscope to be displayed on the screen of a cathode-ray tube monitor, and to be recorded on video tape.

The representation of FIG. 1 illustrates various electronic units which are included in the arthroscopic assembly of the invention. These units include a video camera electronic unit 10 which is connected to a video camera 12, and which serves to process the video signals from the video camera. The video camera unit 10 is connected to a television monitor 14, and it may also be connected to a video cassette recorder 16.

Each of the units shown in FIG. 1 are known, and are available on the market. For example, the electronic video camera unit 10 and video camera 12 may be of the type presently marketed by Stryker Corporation of Kalamazoo, Mich. The video cassette recorder may be any appropriate commercially available recorder using, for example, three-quarter inch or one-half inch tape.

As will be described, the television monitor 14 is mounted on an appropriate movable stand which can be moved to be directly adjacent to the operating surgeon. For that reason, and since the surgeon is viewing the image from a few feet away, an inexpensive compact 12 inch monitor may be used instead of the more massive 19 inch unit which is commonly used at the present.

Figure 2B:
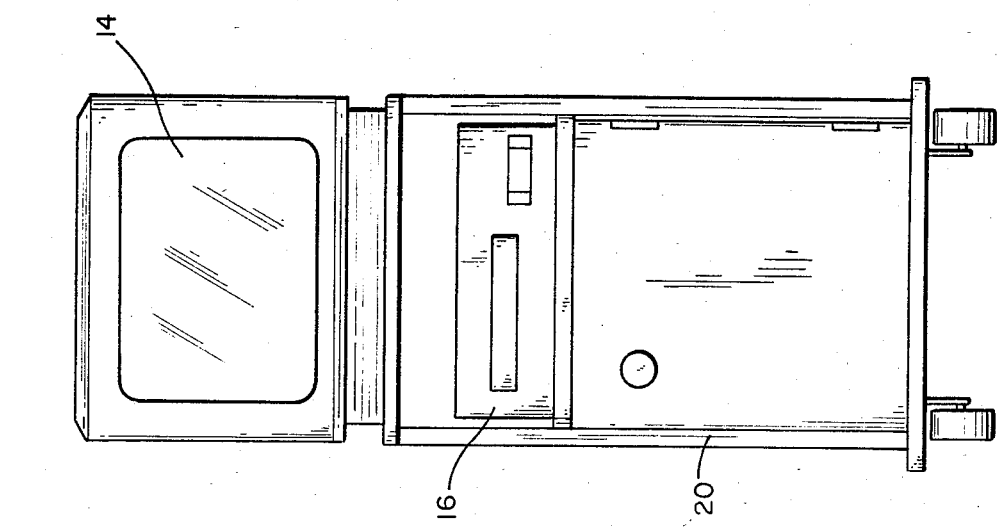
FIG. 2B is a front view (taken along the lines 2B—2B of FIG. 2A) of a stand for the cathode-ray tube monitor and for the video cassette recorder which are included in the video components of FIG. 1.
Figure 2A:
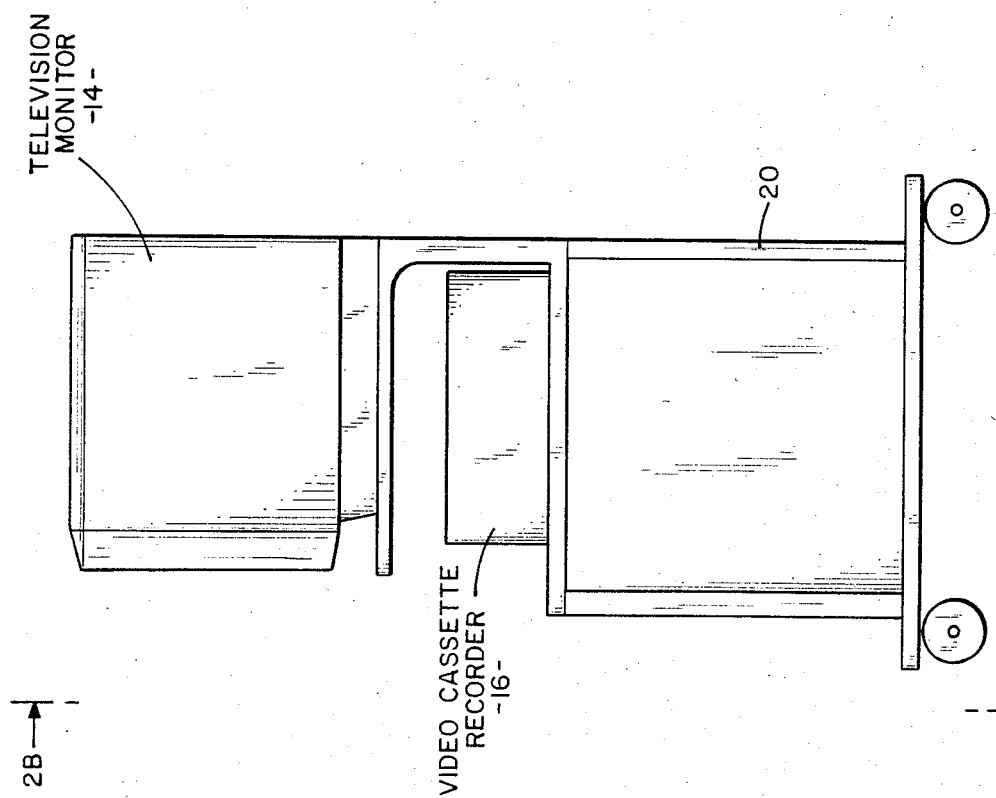
FIG. 2A is a side elevation.

As shown in FIGS. 2A and 2B, the monitor 14 and video cassette recorder 16 may both be supported on a movable stand 20. As mentioned above, stand 20 may be positioned to be relatively close to the operating system so that he may conveniently view the image on the screen of the television monitor.

The camera electronic unit 10 may be mounted in a cabinet 22 on a separate movable stand 24, as shown in FIGS. 3A and 3B. The movable stand 24 may be positioned directly adjacent to the operating table. The video camera unit 10 is connected to the video cassette recorder 16 and television monitor 14 on stand 20 by appropriate cables that may extend along the the floor, so as to obviate any need for an overhead boom.

A Holder 26 is provided at the top of the stand 24, and this holder serves as a support for the arthroscope and video camera when not in use. The stand is positioned so that the surgeon can readily pick up the arthroscope and camera during the procedure. Electric outlets 30 and 32 are provided on the stand 24. Outlet 32, for example, connects with the video camera unit 10 in the stand, and provides connections to the video camera, whereas outlet 30 provides electrical energy for the arthroscopic light which is used in conjunction with the arthroscopic, as will be described. The arthroscopic light may be stored in a second cabinet 34 on the stand 24 when not in use. The use of a holder 26 for holding the camera and arthroscope when not in use is advantageous since with a holder there is less danger of accidentally dropping the camera. The outlets 30 and 32 eliminate the need for long cords which require the use of a boom, and which are cumbersome to use, as discussed above.

Figure 4:
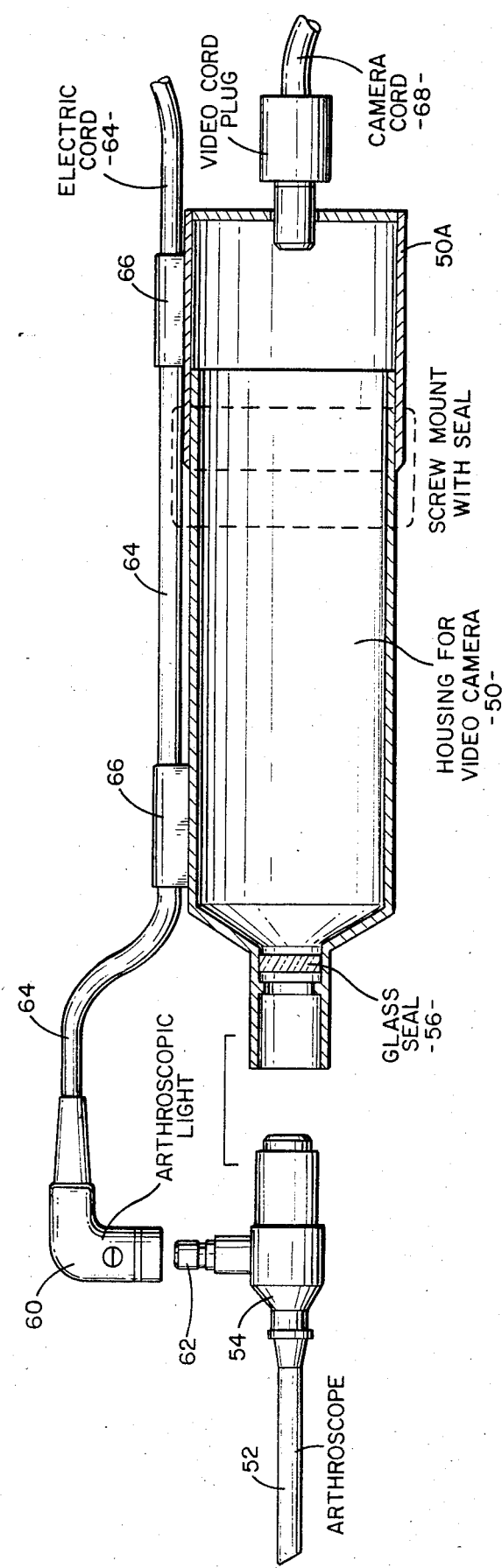
FIG. 4 is a side view, partly in section, of an arthroscope constructed in accordance with the teachings of the present invention, and adapted to be pluggged into one end of a video camera housing so that the arthroscopic images may be sensed by the video camera in the housing.

In accordane with the present invention, the video camera 12, which, as shown in FIG. 1 has an elongated tubular configuration, is removably contained within a housing 50 (FIG. 4). The housing 50 has an elongated tubular shape. It is formed of appropriate material, such as stainless steel whcih may be autoclaved for repeated use during each day. The housing includes a tubular cap 50A may be unscrewed to allow for the insertion of the video camera 12. Once the video camera is inserted into the housing, the cap 50A screws into the housing as a water-tight seal. An arthroscope 52 is detachably received in a mounting bracket 54 which, in turn, is detachably received in a socket on the forward end of housing 50 in a bayonet plug relationship. The arthroscope eyepiece is removed from the arthroscope 52, and the end of the arthroscope is directly coupled to the interior of the housing 50 through the mounting bracket 54. A glass seal 56 effectively seals the interior of the housing.

An arthroscopic light 60 is provided which detachably receives a plug 62 on mounting bracket 54. An electric cord 64 is connected to the arthroscopic light, and it is supported on the housing by appropriate clips 66.

When the arthroscopic light 60 receives plug 62, it supplies light for the arthroscope 52. Electric cord 64 receives its electric energy from outlet 30 on movable stand 24 of FIG. 3B. Arthroscope 52 is detachable from mounting bracket 54 to permit other arthroscopes to be used with, for example, straight, 30°, 70°, and even 90° lenses. The fact that the arthroscopic light 60 is coupled to the mounting bracket 54 means that the arthroscopes can be replaced easily without danger of contamination, and without any need to decouple the light 62 before such a change can be made, as is the case in the prior art arrangements.

The camera cord 68 plugs into the cap 50A of the housing and is connected to the camera contained in the housing. Camera cord 68 is connected to the camera outlet 32 of FIG. 3B.

As mentioned above, since the arthroscope 52 is designed for use with the video housing, there is no need for an eyepiece. The arthroscope, accordingly, is more compact than the prior art devices, and may be of the order of four inches in length. The arthroscope 52, moreover, can be produced more inexpensively than the prior art arthroscopes.

It will be appreciated that while a particular embodiment of the invention has been shown and described, modifications may be made. It is intended in the claims to cover all modifications which come within the true spirit and scope of the invention.

What is claimed is:

1. A video arthroscope assembly comprising: a video camera; a housing for removably receiving said video camera with the video camera being enclosed within said housing, said housing being formed of a material capable of being sterilized; a video camera electronic unit for receiving and amplifying video signals from said video camera; a television monitor; cable means connecting said television monitor to said video camera electronic unit; a first electric cord connecting said video camera electronic unit to said video camera in said housing for introducing video signals from said camera to said electronic unit to be processed therein; an arthroscope; a mounting bracket for detachably receiving said arthroscope, said mounting bracket being detachably mounted to one end of said housing and optically coupled to the interior of said housing for introducing optical images from the arthroscope to the video camera within said housing to be converted by the video camera into corresponding video signals; an arthroscopic light; and means for detachably attaching said arthroscopic light to said mounting bracket so that light from said arthroscopic light may pass through said mounting bracket to said arthroscope.

2. The video arthroscope assembly defined in claim 1, in which said housing has an elongated tubular shape.

3. The video arthroscope assembly defined in claim 2, in which said housing is formed of stainless steel.

4. The video arthroscope assembly defined in claim 2, and which includes plug and receptacle means mounted at the other end of said housing for detachably connecting said first electric cord to said video camera.

5. The video arthroscope assembly defined in claim 2, and which includes a transparent seal mounted at said one end of said housing.

6. The video arthroscope assembly defined in claim 1, and which includes a movable stand for holding said housing, said video camera and said arthroscope when not in use.

7. The video arthroscope assembly defined in claim 1, and which includes a second electric cord connected to said arthroscopic light, a movable stand for holding said housing, said video camera contained in said housing, and said arthroscope, when not in use; and electric outlets mounted on said movable stand for respectively connecting said first electric cord to said video camera electronic unit, and for supplying electric energy to said second electric cord.

8. The video arthroscope assembly defined in claim 6, and which includes a separate movable stand for supporting said television monitor.

9. The video arthroscope assembly defined in claim 8, and which includes a video cassette recorder connected to said video camera electronic unit, said recorder being supported on said separate stand.

10. A video arthroscope assembly comprising: a video camera; a housing for removably receiving said video camera, with the video camera being enclosed within said housing, said housing being composed of material capable of being sterilized; an arthroscope; a mounting bracket for detachably receiving said arthroscope, said mounting bracket being detachably mounted to one end of said housing and optically coupled to the interior of said housing to introduce optical images from the arthorscope to said video camera to be converted thereby into corresponding video signals; an arthroscopic light; and bracket means for detachably attaching said arthroscopic light to said mounting bracket so that light from said arthroscopic light passes through said mounting bracket to said arthroscope.

11. The video arthroscope assembly defined in claim 10, in which said housing has an elongated tubular shape.

12. The video arthroscope assembly defined in claim 11, in which said housing is formed of stainless steel.

13. The video arthroscope assembly defined in claim 11, and which includes a transparent seal mounted at said one end of housing.

* * * * *